United States Patent [19]

Mori et al.

[11] Patent Number: 5,308,820
[45] Date of Patent: May 3, 1994

[54] CATALYST FOR ASYMMETRIC INDUCTION

[75] Inventors: Atsunori Mori; Shohei Inoue, both of Tokyo, Japan

[73] Assignee: Sumitomo Chemical Company, Limited, Osaka, Japan

[21] Appl. No.: 5,117

[22] Filed: Jan. 15, 1993

[30] Foreign Application Priority Data

Mar. 18, 1992 [JP] Japan .................................. 4-062249

[51] Int. Cl.$^5$ .............................................. B01J 31/02
[52] U.S. Cl. ..................................... 502/167; 502/171
[58] Field of Search ................................. 502/167, 171

[56] References Cited

FOREIGN PATENT DOCUMENTS 0271868  6/1988  European Pat. Off. .
0420658  4/1991  European Pat. Off. .

OTHER PUBLICATIONS

A. Mori et al., "Peptide-Metal Complex . . . Catalyst. A Catalytic Enantioselective Cyanohydrin Synthesis", *Tetrahedron Letters,* vol. 32, No. 34, 1991 (no month available), pp. 4333-4336.

M. Hayashi et al., "Enantioselective Trimethylsilylcyanation of Some Aldehydes by Chiral Titanium Schiff's Base Complexes", *J. Chem. Soc., Chem. Commun.,* 1991 (no month available), pp. 1752-1753.

Inoue et al., "Peptide-Metal Complex as an Asymmetric Catalyst. A Catalytic Enantioselective Cyanohydrin Synthesis," *Tetrahedron Letters,* vol. 32, No. 34, Aug. 19, 1991.

Inoue et al., "Asymmetric Addition of Hydrogen Cyanide to Substituted Benzaldehydes Catalyzed by a Synthetic Cyclic Peptide, Cyclo((S)-Phenylalanyl-(S)-Histidyl)," *Bulletin of the Chemical Society of Japan,* vol. 59, pp. 893-895, Mar. 1986.

Inoue et al., "A Novel Rate Enhancement in Titanium and Zirconium Alkoxide Mediated Cyano Group Transfers by the Addition of a Salicylal Type Schiff Base, dl-3-(2-Hydroxy-1-Naphthylidene)-Imino-ε-Caprolactam," *Chemistry Letters,* No. 1, pp. 145-148, 1991.

Inoue et al., "Peptide-Titanium Complex and Catalyst for Asymmetric Addition of Hydrogen Cyanide to Aldehyde," *Journal of the American Chemical Society,* vol. 114, No. 21, pp. 7969-7975, 1992.

Inoue et al., "Enantioselective Addition of Diethylzinc to Aldehydes Catalyzed by α-Amino Acid Amides," *Synlett,* No. 5, pp. 427-428, May 1992.

*Primary Examiner*—Patrick P. Garvin
*Attorney, Agent, or Firm*—Sughrue, Mion, Zinn, Macpeak & Seas

[57] ABSTRACT

A catalyst for asymmetric induction is provided which comprises an amino acid amide derivative represented by the formula [I]:

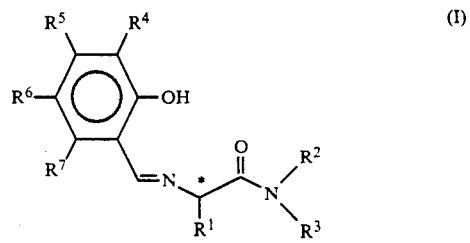

wherein $R^1$ represents an isopropyl group, etc., $R^2$ and $R^3$ are the same or different and each represents a lower alkyl group, etc., $R^4$ represents a chlorine atom, etc., $R^5$, $R^6$ and $R^7$ are the same or different and each represents a hydrogen atom, etc., and * denotes an obosolute configuration of S or R, and a titanium (IV) alkoxide.

Optically active cyanohydrins are obtained in high yield and at high purity by addition of hydrogen cyanide to aldehyde compounds in the presence of the above mentioned catalyst.

18 Claims, No Drawings

CATALYST FOR ASYMMETRIC INDUCTION

The present invention relates to a catalyst for asymmetric induction. More particularly, it relates to a catalyst useful for preparation of optically active cyanohydrins by addition of hydrogen cyanide to aldehyde compounds.

The inventors have previously reported that (R)-cyanohydrins are obtained by asymmetric addition reaction of hydrogen cyanide to aldehyde compounds in the presence of cyclo-(S-phenylalanyl-S-histidyl) [Inoue et al., J. Chem. Soc. Chem. Commun., 229 (1981), Bull. Chem. Soc. Jpn., 59,893 (1986)]. For example, (R)-mandelo-nitrile is obtained at a relatively high purity and in a high yield by allowing benzaldehyde to react with hydrogen cyanide in the presence of cyclo-(S-phenylalanyl-S-histidyl).

In the course of research on asymmetric induction reaction by dipeptide derivatives, the inventors have found that metal complexes of amino acid derivatives represented by the following formula [I] have an excellent catalytic activity for asymmetric induction and thus the present invention has been accomplished.

That is, the present invention provides a catalyst for asymmetric induction comprising an amino acid amide derivative represented by the formula [I]:

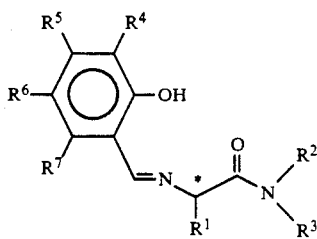

(I)

[wherein $R^1$ represents an isopropyl group, an isobutyl group, a sec-butyl group, a tert-butyl group, a phenyl group or a benzyl group, $R^2$ and $R^3$ are the same or different and each represents a lower alkyl group, (e.g., $C_1$–$C_4$ alkyl groups such as methyl, ethyl, isopropyl and butyl), a $C_3$–$C_8$ cycloalkyl group, (e.g., cyclopentyl and cyclohexyl), an unsubstituted or substituted phenyl group (wherein, as the substituent, mention may be made of halogen atoms such as a fluorine atom, a chlorine atom and a bromine atom, $C_1$–$C_4$ alkyl groups such as methyl and ethyl, and $C_1$–$C_4$ alkoxy groups such as methoxy and ethoxy), or a hydrogen atom, or $R^2$ and $R^3$ may be bonded together at their terminals to form a $C_3$–$C_7$ alkylene group, (e.g., butylene, pentylene and $CH_2CH_2OCH_2CH_2$) which may have hetero atoms, (e.g., an oxygen atom and a sulfur atom); $R^4$ represents a chlorine atom, a bromine atom, an iodine atom, a lower alkyl group, (e.g., $C_1$–$C_4$ alkyl groups such as methyl, ethyl, propyl, isopropyl and tert-butyl), or an unsubstituted or substituted phenyl group (wherein, as the substituent, mention may be made of halogen atoms such as a fluorine atom, a chlorine atom and a bromine atom, $C_1$–$C_4$ alkyl groups such as methyl and ethyl, and $C_1$–$C_4$ alkoxy groups such as methoxy and ethoxy); $R^5$, $R^6$, and $R^7$ are the same or different and each represents a hydrogen atom, a halogen atom, (e.g., a fluorine atom, a chlorine atom, a bromine atom or an iodine atom), a methyl group or a methoxy group or $R^5$ and $R^6$ or $R^6$ and $R^7$ are bonded together at their terminals to form CH=CH—CH=CH or $OCH_2O$, and * denotes an abosolute configuration of S or R], and a titanium (IV) alkoxide. The present invention further provides a process for preparing optically active cyanohydrins by addition of hydrogen cyanide to aldehyde compounds, in the presence of the above catalyst.

As the amino acid amide derivatives there may be usually used those wherein $R^4$ is a phenyl group and $R^5$, $R^6$ and $R^7$ are hydrogen atoms all and those wherein $R^4$ and $R^6$ are a chlorine atom, a bromine atom or an iodine atom and $R^5$ and $R^7$ are hydrogen atoms.

The amino acid amide derivatives represented by the formula [I] used for the catalyst of the present invention are prepared, for example, by condensation of salicylaldehyde derivatives and amino acid amides as shown in the following scheme.

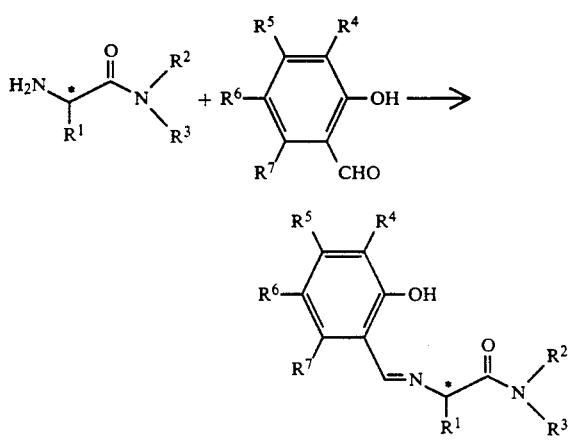

wherein $R^1$, $R^2$, $R^3$, $R^4$, $R^5$, $R^6$, $R^7$ and * are the same as defined above.

The amino acid amides to be condensed with the salicylaldehyde derivatives in the above scheme are prepared by conventional processes. That is, N-benzyloxycarbonyl-S-valine, N-benzyloxycarbonyl-S-leucin, N-benzyloxycarbonyl-S-isoleucin, N-benzyloxycarbonyl-S-tert-leucin, N-benzyloxycarbonyl-S-phenylglycine, N-benzyloxycarbonyl-S-phenylalanine or the corresponding R-isomers thereof are converted to the corresponding amide derivatives and then the amide derivatives are subjected to hydrogenolysis in the presence of palladium/carbon.

The titanium (IV) alkoxides (such as titanium (IV) $C_1$–$C_4$ alkoxides such as methoxide, ethoxide, isopropoxide, propoxide and butoxide) used as a component of the present catalyst are, for example, lower alkoxides of titanium (IV) such as titanium (IV) tetraethoxide, titanium (IV) tetraisopropoxide, titanium (IV) tetrapropoxide and titanium (IV) tetrabutoxide. The molar ratio of the compound represented by the formulae [I] and the titanium (IV) alkoxide used is generally in the range from about 1:0.5 to about 1:2, preferably in the range from 1:1 to 1:2.

For example, when Ps—S—Val—NHCy, (an amino acid amide derivative compound represented by the formulae [I] wherein $R^1$ is an isopropyl group, $R^2$ is a cyclohexyl group, $R^3$ is a hydrogen atom, $R^4$ is a phenyl group, $R^5$, $R^6$ and $R^7$ are hydrogen atoms and the absolute configuration is S-isomer), and titanium (IV) tetraethoxide are used as the catalyst of the present invention, (S)-mandelonitrile is produced by a reaction of benzaldehyde and hydrogen cyanide in the presence of the catalyst. When Dbs—S—Val—Pip, (a compound represented by the formula [I] wherein $R^1$ is an isopropyl group, $R^2$ and $R^3$ are pentylene groups, $R^4$ and $R^6$ are bromine atoms, $R^5$ and $R^7$ are hydrogen atoms and the absolute configuration is S-isomer), and titanium (IV) tetraethoxide are used as the catalyst of the present invention, (S)-mandelonitrile is produced. Thus, the catalyst of the present invention is very useful as a catalyst for producing various optically active cyanohydrins which are useful as intermediates in the preparation of pharmaceuticals, agrochemicals such as pyrethroid insecticides, perfumes or the like.

As substrate compounds to which the catalyst of the present invention can work, mention may be made of, in addition to the above-mentioned benzealdehyde, aromatic aldehydes such as p-methylbenzaldehyde, m-methoxybenzaldehyde, naphthoaldehyde, furfural and m-phenoxybenzaldehyde optionally substituted with one or two halogen atoms such as a fluorine atom, a chlorine atom and a bromine atom, aliphatic aldehydes such as heptanal and alicyclic aldehydes such as cyclohexanecarboaldehyde.

When the catalyst of the present invention is used for the asymmetric synthesis of optically active cyanohydrins, 1-15 mol % based on the aldehyde compound is enough to attain the object. The reaction is usually carried out by allowing aldehyde compounds to react with hydrogen cyanide in an amount of 1-5 moles for 1 mole of the aldehyde compounds in inert solvents such as toluene, methylene chloride, ethyl ether and isopropyl ether at a temperature in the range from $-80°$ C. to room temperature. After the reaction is over, the reaction mixture is poured into a dilute hydrochloric acid-methanol solution. After excess hydrogen cyanide is removed under reduced pressure, the solution is subjected to the usual after-treatment to obtain a desired optically active cyanohydrin.

The present invention is further explained in the following examples.

EXAMPLE 1

0.05 mmol of Ps—S—Val—NH—Cy (as defined above) was suspended in 3 ml of toluene at room temperature under argon atmosphere, and 0.05 mmol of titanium (IV) tetraethoxide was added to the suspension. After being stirred for 30 minutes, the reaction mixture was cooled to $-78°$ C. and 0.5 mmol of benzaldehyde and 0.75 mmol of hydrogen cyanide were added thereto. The reaction mixture was further stirred at $-40°$ C. for 5 hours and then poured into a dilute hydrochloric acid-methanol solution. The excessive amount of hydrogen cyanide was removed under reduced pressure and mandelonitrile was recovered from the organic layer. Yield: 81%. The product contained the R- and S-isomers at a ratio of 20:80.

The yield was calculated from integrating intensities of the $^1H$—NMR spectrum of crude product, and the ratio of the R- and S-isomers was determined by the integrating intensities of the signals corresponding to the methyne protons on the $^1H$—NMR spectrum after the product was converted to a pair of diastereomers of the corresponding menthyl carbonate according to the usual method. [Tanaka et al., J. Org. Chem., 55, 181 (1990); Mori et al., Chem. Lett., 1989, 2119].

EXAMPLE 2

Example 1 was repeated except that the stirring was carried out at $-60°$ C. for 19 hours in place of $-40°$ C. and 5 hours, to obtain mandelonitrile. Yield: 81%. The product contained the R- and S-isomers at a ratio of 15:85.

EXAMPLE 3

Example 1 was repeated except that Ps—S—Val—Pip (which is the compound represented by the formula [I]; $R^1$, an isopropyl group; $R^2$ and $R^3$, pentylene groups; $R^4$, a phenyl group; $R^5$, $R^6$ and $R^7$, hydrogen atoms and the absolute configuration being S-isomers) was used in place of the Ps—S—Val—NHCy, and the stirring was carried out at $-60°$ C. for 37 hours in place of $-40°$ C. and 5 hours, to obtain mandelonitrile. Yield: 73%. The product contained the R- and S-isomers at a ratio of 8.5:91.5.

EXAMPLE 4

Example 1 was repeated except that Dbs—S—Val—Pip (as defined above) was used in place of the Ps—S—Val—NHCy and the stirring was carried out at $-60°$ C. for 34 hours in place of $-40°$ C. and 5 hours, to obtain mandelonitrile. Yield: 93%. The product contained the R- and S-isomers at a ratio of 6.5:93.5.

EXAMPLE 5

Example 4 was repeated except that m-methoxybenzaldehyde was used in place of the benzaldehyde and the stirring was carried out at $-60°$ C. for 31 hours in place of $-60°$ C. and 34 hours, to obtain α-hydroxy-(m-methoxy)acetonitrile. Yield: 94%. The product contained the R- and S-isomers at a ratio of 3.5:96.5.

EXAMPLE 6

Example 4 was repeated except that o-methylbenzaldehyde was used in place of the benzaldehyde and the stirring was carried out at $-60°$ C. for 31 hours in place of $-60°$ C. and 34 hours, to obtain α-hydroxy-(o-tolyl) acetonitrile. Yield: 93%. The product contained the R- and S-isomers at a ratio of 4:96.

EXAMPLE 7

Example 4 was repeated except that 2-naphthoaldehyde was used in place of the benzaldehyde and the stirring was carried out at $-60°$ C. for 24 hours in place of $-60°$ C. and 34 hours, to obtain α-hydroxy-(2-naphthyl)acetonitrile. Yield: 63%. The product contained the R-and S-isomers at a ratio of 13:87.

EXAMPLE 8

Example 4 was repeated except that cinnamaldehyde was used in place of the benzaldehyde and the stirring was carried out at $-60°$ C. for 24 hours in place of $-60°$ C. and 34 hours, to obtain -hydroxy-(styryl-)acetonitrile. Yield: 51%. The product contained the R- and S-isomers at a ratio of 17.5:82.5 according to high performance liquid chromatography using an optically active column SUMICHIRAL OA-4100 manufactured by Sumika Chemical Analysis Service Ltd.

EXAMPLE 9

Example 3 was repeated except that m-methoxybenzaldehyde was used in place of the benzaldehyde and the stirring was carried out at $-60°$ C. for 36 hours in place of $-60°$ C. and 37 hours, to obtain α-hydroxy-(m-methoxyphenyl)-acetonitrile. Yield: 73%. The product contained the R- and S-isomers at a ratio of 9.5:90.5.

EXAMPLE 10

Example 3 was repeated except that 2-naphthoaldehyde was used in place of the benzaldehyde and the stirring was carried out at −60° C. for 42 hours in place of −60° C. and 37 hours, to obtain α-hydroxy-(2-naphthyl)acetonitrile. Yield: 93%. The product contained the R-S-isomers at a ratio of 14:86.

EXAMPLE 11

Example 3 was repeated except that o-methylbenzaldehyde was used in place of the benzaldehyde and the stirring was carried out at −60° C. for 42 hours in place of −60° C. and 37 hours, to obtain α-hydroxy-(o-tolyl)acetonitrile. Yield: 83%. The product contained the R-and S-isomers at a ratio of 3:97.

EXAMPLE 12

Example 3 was repeated except that furfural was used in place of the benzaldehyde and the stirring was carried out at −60° C. for 36 hours in place of −60° C. and 37 hours, to obtain α-hydroxy-furfurylnitrile. Yield: 83%. The product contained the R- and S-isomers at a ratio of 21.5:78.5.

EXAMPLE 13

Example 3 was repeated except that heptanal was used in place of the benzaldehyde and the stirring was carried out at −60° C. for 12 hours in place of −60° C. and 37 hours, to obtain 2-hydroxyoctanenitrile. Yield: 97%. The product contained the R- and S-isomers at a ratio of 43.5:56.5. In this example, the ratio of R- and S-isomers was determined by gas chromatography after the product was converted to a pair of diastereomers of the corresponding (+)-1-methoxy-1-phenyl-2,2,2-trifluoro-propionic acid ester.

Examples of preparation of the amino acid amide derivatives represented by the formula [I] are shown below.

REFERENCE EXAMPLE 1

Preparation of N-(3-phenylsalicylidene)-(S)-valine cyclohexyl amide

First, 3-phenylsalicylamide was prepared from 3-phenylsalicylic acid in the following manner. Lithium aluminum hydride (1.52 g, 40 mmol) was added gradually and little by little to a solution of 3-phenylsalicylic acid (4.28 g, 20 mmol) in anhydrous tetrahydrofuran (THF) (100 ml) at −20° C. The mixture was slowly allowed to warm to room temperature. The mixture was stirred for 12 hours and heated under refluxing for 1 hour. To this mixture were added 2-propanol (20 ml), methanol (40 ml) and water (40 ml) in order to decompose excess lithium aluminum hydride. Most of the organic solvents were removed under reduced pressure and the residual aqueous layer was extracted twice with ether (70 ml). The combined organic layer was dried over $Na_2SO_4$ and concentrated under reduced pressure to obtain a crude product. This was subjected to silica gel column chromatography (eluent; hexane:ethyl acetate=5:1) to obtain 3.06 g (77%) of 2-hydroxy-3-phenylbenzyl alcohol as white solids.

To a solution of 2-hydroxy-3-phenylbenzyl alcohol (2.00 g, 10 mmol) in dioxane (100 ml) was added 2,3-dichloro-5,6-dicyano-1,4-benzoquinone (DDQ) (2.50 g, 11 ml) at room temperature. The reaction mixture immediately became a black solution. This solution was stirred at room temperature for 2 hours and further heated under refluxing for 2 hours. The solvent was removed under reduced pressure to obtain deep-black oily residue. This was subjected to silica gel column chromatography (eluent; hexane:ethyl acetate=4:1) to obtain 1.63 g (82%) of 3-phenylsalicylaldehyde as a light yellow oil.

A solution of carbobenzoxy-(S)-valine (1.26 g, 5 mmol) in anhydrous THF (20 ml) was vigorously stirred and thereto were added triethylamine (0.70 ml, 5 mmol) and isobutyl chloroformate (0.66 ml, 5 mmol) at 0° C. To this mixture was added cyclohexylamine (0.57 ml, 5 mmol) and this mixture was stirred for 2 hours at 0° C. and further for 24 hours at room temperature. The solvent was removed to obtain white crystals. These crystals were dissolved in a mixture of $CH_2Cl_2$ (80 ml) and water (30 ml). The organic layer was washed with 0.5M boric acid, a saturated aqueous sodium chloride solution, a saturated aqueous sodium hydrogencarbonate solution, a saturated aqueous sodium chloride solution and water (50 ml each) in succession, dried over $Na_2SO_4$ and concentrated under reduced pressure to obtain crude carbobenzoxy-(S)-valine cyclohexylamide (1.45 g, 87%), which was used as it was for the following reaction.

The carbobenzoxy-(S)-valine cyclohexylamide (0.33 g, 1 mmol) was dissolved in methanol (30 ml) and the solution was stirred at room temperature for 3 hours in the presence of 5% palladium-carbon (30 mg) under a hydrogen gas atmosphere. After the reaction was over, the palladium-carbon catalyst was filtered off to obtain a colorless solution. To this solution was added 3-phenylsalicylaldehyde (0.22 g, 1.1 mmol). This solution was stirred at room temperature for 24 hours and concentrated under reduced pressure to obtain yellow solids. These solids were subjected to silica gel column chromatography (eluent; hexane:ethyl acetate=5:1) to obtain 0.29 g (76%) of the desired N-(3-phenylsalicylidene)-(S)-valine cyclohexylamide which was further recrystallized from ether. m.p. 87.0°–89.5° C. $[\alpha]^{26}_D+158.3°$ (c 1.02, $CHCl_3$)

REFERENCE EXAMPLE 2

Preparation of N-(3-phenylsalicylidene)-(S)-valine piperizide

The desired product was prepared in the same manner as Reference Example 1. That is, carbobenzoxy-(S)-valine (3.77 g, 15 mmol) was coupled with piperidine (1.49 ml, 15 mmol) to obtain crude carbobenzoxy-(S)-valine piperizide as a viscous liquid (4.46 g, 93%). This product (0.32 g, 1 mmol) was hydrogenated and then condensed with 3-phenylsalicylaldehyde (0.20 g, 1 mmol) to obtain 0.30 g (68%) of the desired N-(3-phenylsalicylidene)-(S)-valine piperizide, which was further recrystallized from ether. m.p. 140.1°–141.0° C. $[\alpha]^{26}_D+90.1°$(c 0.99, $CHCl_3$)

REFERENCE EXAMPLE 3

Preparation of N-(3,5-dibromosalicylidene)-(S)-valine piperizide

The desired product was prepared in the same manner as the latter half procedure of Reference Example 1. That is, carbobenzoxy-(S)-valine piperizide (0.32 g, 1 mmol) was hydrogenated and then condensed with 3,5-dibromosalicylaldehyde (0.42 g, 1.5 mmol) to obtain 0.30 g (68%) of the desired N-(3,5-dibromosalicylidene)-(S)-valine piperizide, which was further recrystallized from methanol. m.p. 143.2°–145.4° C. $[\alpha]^{26}_D +50.1°$ (c 0.97, CHCl$_3$)

The catalysts for asymmetric induction of the present invention are useful ones which give high yield and high optical purity in production of optically active cyanohydrins by the addition of hydrogen cyanide to aldehyde compounds.

What is claimed is:

1. A catalyst for asymmetric induction comprising the amino acid amide derivative defined below and a titanium (IV) alkoxide, said amino acid amide derivative being represented by the formula (I):

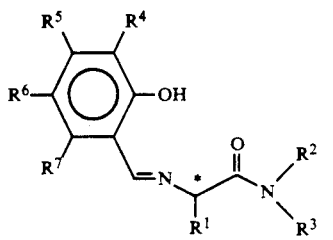

wherein $R^1$ represents an isopropyl group, an isobutyl group, a sec-butyl group, a tert-butyl group, a phenyl group or a benzyl group, $R^2$ and $R^3$ are the same or different and each represents a lower alkyl group, a $C_3$-$C_8$ cycloalkyl group, an unsubstituted or substituted phenyl group or a hydrogen atom or $R^2$ and $R^3$ may be combined to form a $C_3$-$C_7$ alkylene group, $R^4$ represents a chlorine atom, a bromine atom, an iodine atom, a lower alkyl group or an unsubstituted or substituted phenyl group, $R^5$, $R^6$ and $R^7$ are the same or different and each represents a hydrogen atom, a halogen atom, a methyl group or a methoxy group or $R^5$ and $R^6$ or $R^6$ and $R^7$ may be combined to form CH=CH—CH=CH or OCH$_2$O and * denotes an absolute configuration of S or R, wherein the substituted phenyl group of $R^2$, $R^3$ and $R^4$ each contains a substituent selected from the group consisting of a halogen atom, a $C_1$-$C_4$ alkyl group and a $C_1$-$C_4$ alkoxy group.

2. A catalyst according to claim 1, wherein the amino acid amide derivative and the titanium (IV) alkoxide are present in the catalyst in a molar ratio of from about 1:0.5 to about 1:2.

3. A catalyst for asymmetric induction comprising the amino acid amide derivative represented by the formula,

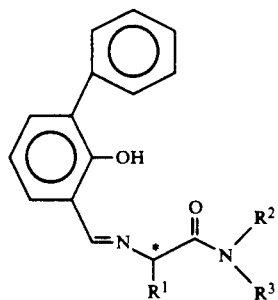

wherein $R^1$, $R^2$, and $R^3$ and * are the same as those defined in claim 1, and titanium (IV) alkoxide, wherein the substituted phenyl group of $R^2$ and $R^3$ each contains a substituent selected from the group consisting of a halogen atom, a $C_1$-$C_4$ alkyl group and a $C_1$-$C_4$ alkoxy group.

4. A catalyst for asymmetric induction comprising the amino acid amide derivative represented by the formula,

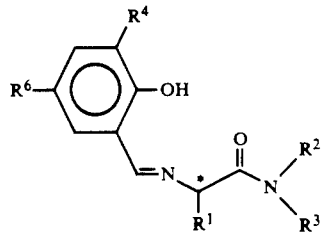

wherein $R^4$ and $R^6$ are the same or different, and each represents a chlorine atom, a bromine atom or an iodine atom, and $R^1$, $R^2$, $R^3$ and * are the same as those defined in claim 1, and a titanium (IV) alkoxide, wherein the substituted phenyl group of $R^2$ and $R^3$ each contains a substituent selected from the group consisting of a halogen atom, a $C_1$-$C_4$ alkyl group and a $C_1$-$C_4$ alkoxy group.

5. A catalyst according to claim 1, wherein the titanium (IV) alkoxide is a titanium (IV) $C_1$-$C_4$ alkoxide.

6. A catalyst according to claim 5, wherein the titanium (IV) $C_1$-$C_4$ alkoxide is selected from the group consisting of titanium (IV) tetramethoxide, titanium (IV) tetraethoxide, titanium (IV) tetraisopropoxide, titanium (IV) tetrapropoxide and titanium (IV) tetrabutoxide.

7. A catalyst according to claim 2, wherein the molar ratio of amino acid derivative to titanium (IV) alkoxide is from 1:1 to 1:2.

8. A catalyst according to claim 3, wherein the amino acid amide derivative and the titanium (IV) alkoxide are present in the catalyst in a molar ratio of from about 1:0.5 to about 1:2.

9. A catalyst according to claim 8, wherein the molar ratio of amino acid derivative to titanium (IV) alkoxide is from 1:1 to 1:2.

10. A catalyst according to claim 3, wherein the titanium (IV) alkoxide is a titanium (IV) $C_1$-$C_4$ alkoxide.

11. A catalyst according to claim 10, wherein the titanium (IV) $C_1$-$C_4$ alkoxide is selected from the group consisting of titanium (IV) tetramethoxide, titanium (IV) tetraethoxide, titanium (IV) tetraisopropoxide, titanium (IV) tetrapropoxide and titanium (IV) tetrabutoxide.

12. A catalyst according to claim 4, wherein the amino acid amide derivative and the titanium (IV) alkoxide are present in the catalyst in a molar ratio of from about 1:0.5 to about 1:2.

13. A catalyst according to claim 12, wherein the molar ratio of amino acid derivative to titanium (IV) alkoxide is from 1:1 to 1:2.

14. A catalyst according to claim 4, wherein the titanium (IV) alkoxide is a titanium (IV) $C_1$-$C_4$ alkoxide.

15. A catalyst according to claim 14, wherein the titanium (IV) $C_1$-$C_4$ alkoxide is selected from the group consisting of titanium (IV) tetramethoxide, titanium (IV) tetraethoxide, titanium (IV) tetraisopropoxide, titanium (IV) tetrapropoxide and titanium (IV) tetrabutoxide.

16. A catalyst according to claim 1, wherein the $C_3$-$C_7$ alkylene group formed by combining $R^2$ and $R^3$ contains a hetero atom selected from the group consisting of an oxygen atom and sulfur atom.

17. A catalyst according to claim 3, wherein the $C_3$–$C_7$ alkylene group formed by combining $R^2$ and $R^3$ contains a hetero atom selected from the group consisting of an oxygen atom and sulfur atom.

18. A catalyst according to claim 4, wherein the $C_3$–$C_7$ alkylene group formed by combining $R^2$ and $R^3$ contains a hetero atom selected from the group consisting of an oxygen atom and sulfur atom.

* * * * *